United States Patent
Chong

(10) Patent No.: US 7,701,588 B2
(45) Date of Patent: Apr. 20, 2010

(54) SWEPT SOURCE TYPE OPTICAL COHERENT TOMOGRAPHY SYSTEM

(75) Inventor: Changho Chong, Kasugai (JP)

(73) Assignee: Santec Corporation, Komaki (JP)

( * ) Notice: Subject to any disclaimer, the term of this patent is extended or adjusted under 35 U.S.C. 154(b) by 377 days.

(21) Appl. No.: 11/783,424

(22) Filed: Apr. 9, 2007

(65) Prior Publication Data

US 2008/0159468 A1 Jul. 3, 2008

Related U.S. Application Data

(60) Provisional application No. 60/790,785, filed on Apr. 11, 2006.

(51) Int. Cl.
*G01B 9/02* (2006.01)
(52) U.S. Cl. .................................................. 356/497
(58) Field of Classification Search ................ 356/497, 356/479, 489, 511, 512
See application file for complete search history.

(56) References Cited

U.S. PATENT DOCUMENTS 6,879,421 B2 * 4/2005 Clark et al. ................. 359/237

7,336,366 B2 * 2/2008 Choma et al. ............... 356/479

FOREIGN PATENT DOCUMENTS

JP 2004-281733 A 10/2004

OTHER PUBLICATIONS

Li, M. et al., "Top-Emitting Micromechanical VCSEL With A 31.6-nm Tuning Range", IEEE Photonics Technology Letters, Jan. 1998, pp. 18-20, vol. 10, No. 1, IEEE.
Handbook of Optical Coherence Tomography, Edited by Brett E. Bouma, Guillermo J. Tearney, Informa Healthcare; 1st edition, Section 13, "Alternative OCT Techniques", Christoph K. Hitzenberger and Adolf F. Fercher, Nov. 15, 2001, pp. 364-367.
Handbook of Optical Coherence Tomography, Merker Dekker Inc., "Optical Coherence Tomography: Theory", Hee, M., 2002, pp. 41-66.
Maute, M. et al., "MEMS-Tunable 1.55-μm VCSEL With Extended Tuning Range Incorporating A Buried Tunnel Junction", IEEE Photonics Technology Letters, Mar. 2006, pp. 688-690, vol. 18, No. 5, IEEE.

* cited by examiner

*Primary Examiner*—Hwa S. A Lee
(74) *Attorney, Agent, or Firm*—Smith Patent Office

(57) ABSTRACT

A surface emission laser light source is used as a tunable laser light source. Since the surface emission laser light source can realize a broad frequency scanning range at a high speed and in the single mode, a coherent length is longer than that of a multi mode light source. For this reason, when a tomography image is calculated by executing the Fourier transform for an output obtained from an interference optical device, measuring depth can be deepened.

7 Claims, 7 Drawing Sheets

F I G. 4 A
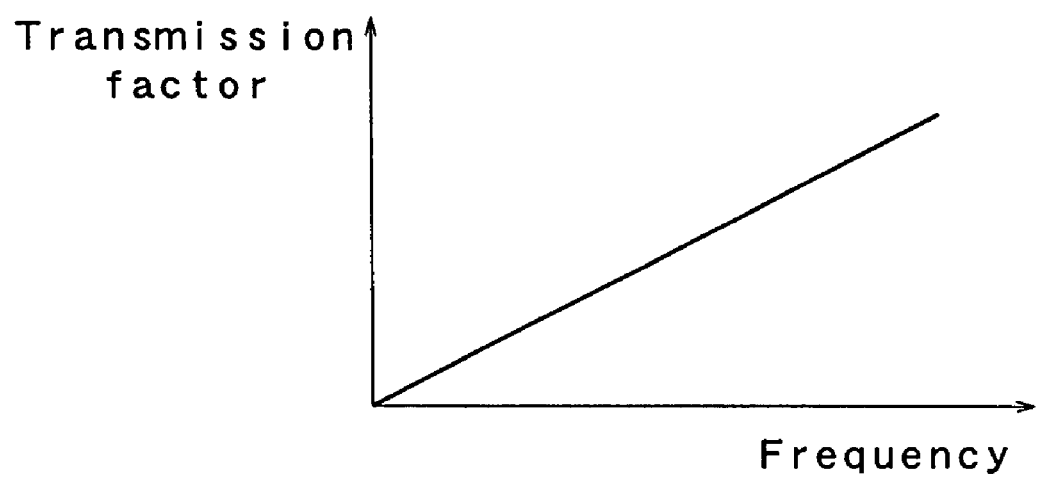
F I G. 4 B
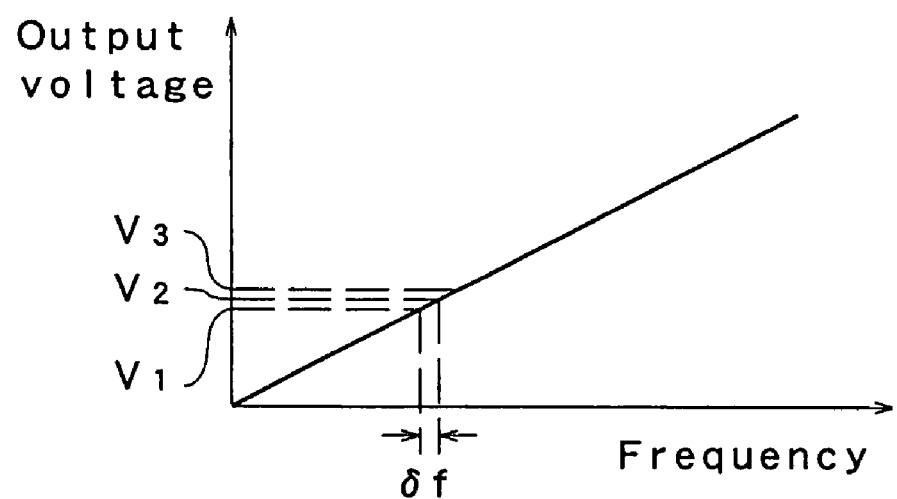

F I G. 5
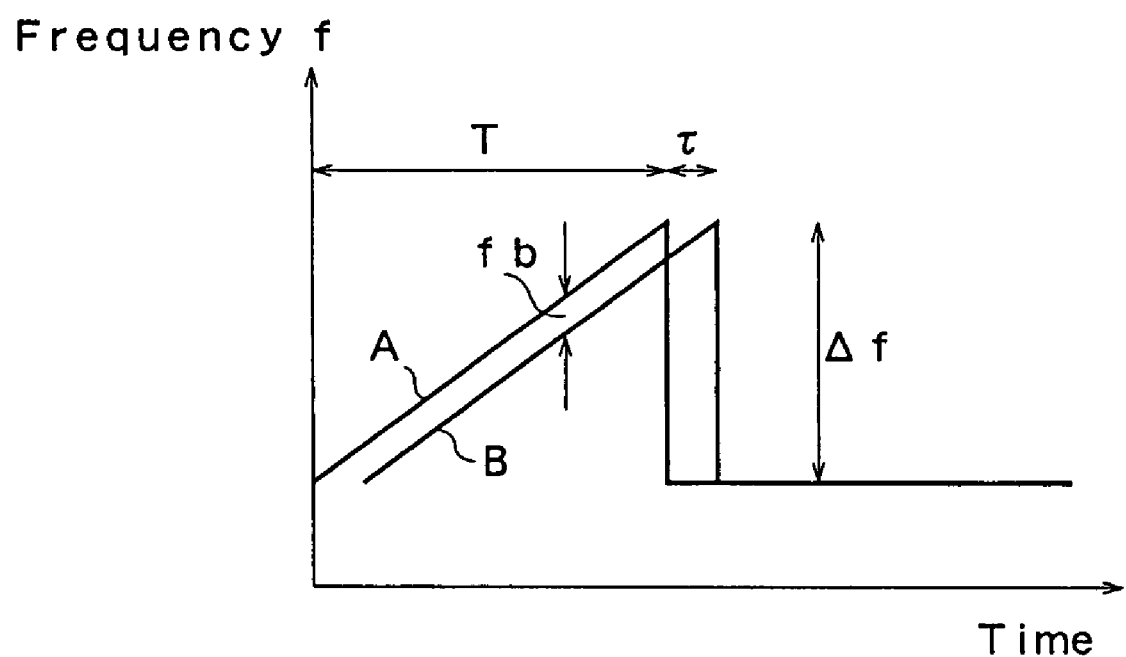

F I G. 6 A
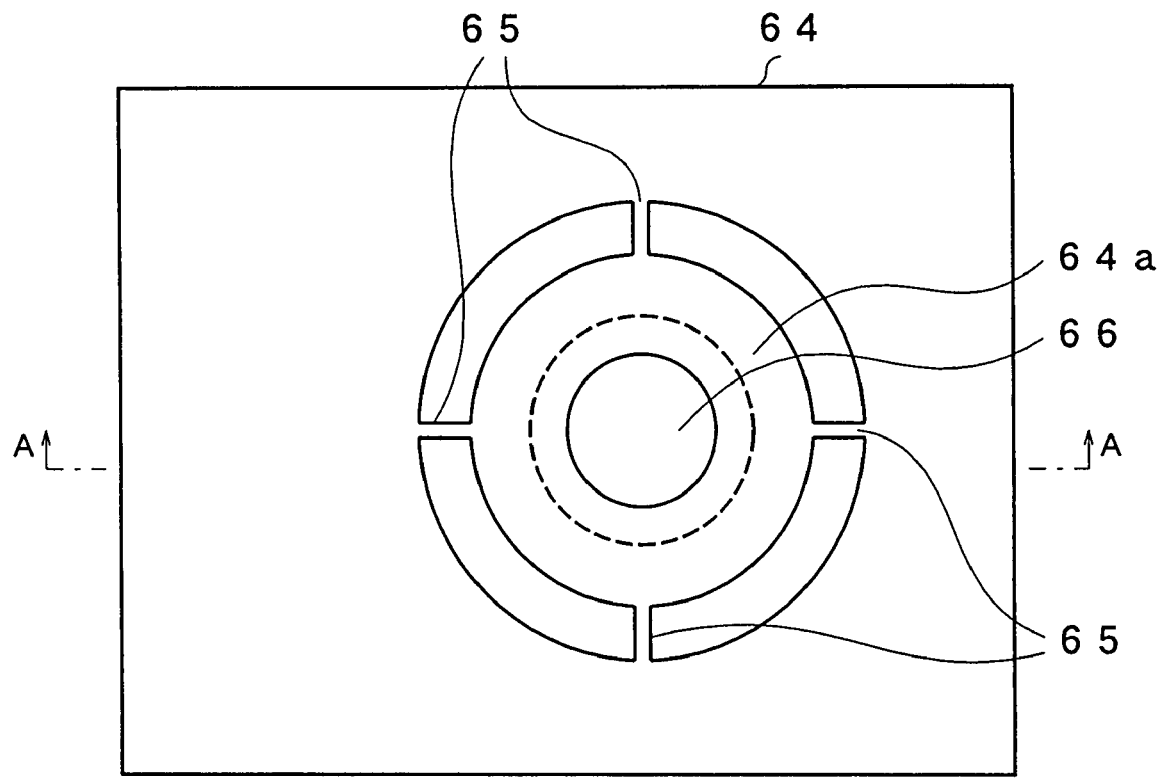
F I G. 6 B
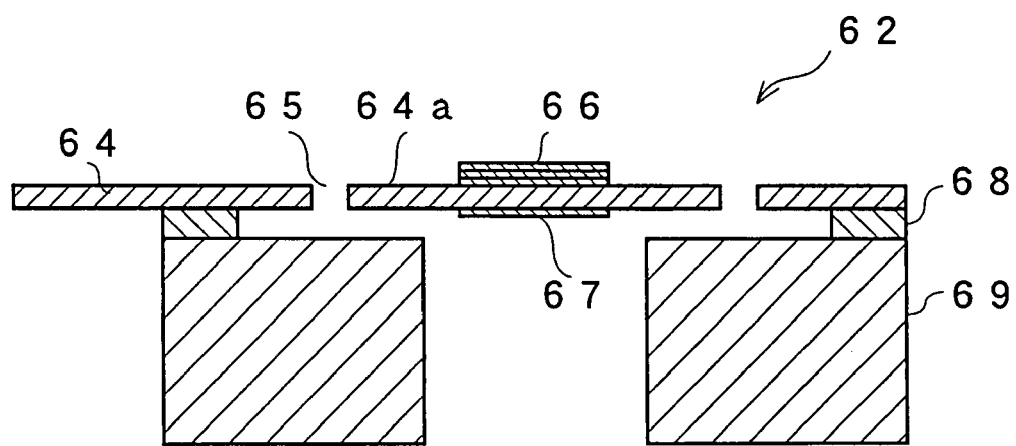

SWEPT SOURCE TYPE OPTICAL COHERENT TOMOGRAPHY SYSTEM

CROSS REFERENCE TO RELATED APPLICATION

This application is a nonprovisional application of U.S. Provisional Patent Application No. 60/790,785 filed on Apr. 11, 2006, currently pending. The disclosure of U.S. Provisional Patent Application No. 60/790,785 is hereby incorporated by reference.

BACKGROUND OF THE INVENTION

1. Field of the Invention

The present invention relates to an optical coherent tomography system, using a tunable surface emission laser source in a single mode.

2. Discussion of the Related Art

In association with advancement of a medical technology such as an endoscopic therapy, a diagnostic measure for non-invasively diagnosing a pathologic tissue in real time has been desired recently. For example, an electronic endoscope using a CCD, and an imaging technology using a CT, an MRI, and an ultrasonic wave are used in a diagnostic approach. The electronic endoscope is only used for observing a biological surface, and the latter diagnostic imaging system has a technical limitation to observe with the micron order resolution. As a technology for complimenting the measure, an optical coherence tomography system (OCT) has drawn attention.

There are two types of the OCT, namely a time domain OCT (TD-OCT) and a frequency domain OCT-(FD-OCT), and there are two types of the FD-OCT, namely a spectrometer type (SD-OCT) and a swept source type (SS-OCT). The time domain OCT sheds broadband light on a living body and analyzes frequencies of interference components in the reflecting light from the living body. However, a signal light from a specific depth cannot be detected with high-sensitivity because reflecting lights from different depths in the interference light overlap each other in this method.

Handbook of Optical Coherence Tomography, p41-43, Mercer Dekker, Inc. 2002 shows a tunable type OCT. The system obtains a tomography image through steps of emitting light to a living body, continuously changes wavelength of the emitted light, makes a reference light and reflecting lights returning from different depths in vivo interfere in an interferometer, and analyzes frequency components of the interfering lights. This technology is expected as an advanced system because a tomography image of extremely high-resolution can be constructed through frequency analysis of signals from inside a body. The SS-OCT using a tunable light source is suitable for practical use in such as endoscope because the SS-OCT has high measurement sensitivity and is strong to dynamic noise. Since the broader a range of wavelength scanning of emitted light is, the higher a range of frequency analysis is, a resolution in depth direction is improved.

As a tunable light source using the SS-OCT, there are a multi-mode tunable laser of the fiber-ring type and an end-face wavelength laser of the integration type. However, the fiber-ring type laser has a limitation of measurement depth, since its spectral width becomes wider with accelerating wavelength scanning speed. As a result of this, a coherence length becomes short. In addition, the fiber-ring type cannot be downsized, and has a problem on mass production. In the end-face wavelength laser of the integration type, a wave length can be varied in the single-mode, while high speed scanning is difficult since a phase control for continuous scanning is complicated.

SUMMARY OF THE INVENTION

The present invention is accomplished with focusing attention on these problems, and intends to provide an optical coherent tomography system having large measuring depth by using a tunable light source which is small, suitable for mass production, and low price, and which is tunable in a single mode.

To solve the problems, an optical tomography system of the present invention comprises: a tunable light source including a tunable surface emission laser for generating laser light and periodically scanning an oscillation wavelength of light; a wavelength monitor for generating trigger signals in equal frequency interval of light of the tunable light source within a period of one scanning of the tunable light source; an interferometer for dividing the light from the tunable light source into a reference light and an emission light, and for generating interference light of reflecting light from an object and the reference light; a light receiving element for receiving interference light from the interferometer and for obtaining a beat signal; and a signal processing part for forming a tomography image of the object by executing the Fourier transform synchronizing a timing with an output from the light receiving element and the trigger signal from the wavelength monitor.

The tunable surface emission laser may include: a bottom DBR layer formed on a substrate; an active layer formed on the bottom DBR layer; a DBR layer formed on the active layer; a movable DBR layer of a cantilever structure formed over the active layer via a gap; and a driving part for driving the movable DBR layer and for changing a cavity length of a cavity formed between the DBR layer on the active layer and the movable DBR layer.

The optical tomography system may further comprise: an optical amplifier for amplifying an optical output of the tunable light source.

The tunable surface emission laser may include an upper mirror part and a bottom substrate, the upper mirror part may include: a diaphragm having an oscillation part supported by hinges; an upper DBR layer provided on the diaphragm for reflecting light; and a handle substrate which faces the diaphragm via a spacer and is formed in circular shape getting rid of a part of the upper DBR layer, and the bottom substrate may include: a bottom DBR layer; an active layer which is provided on a top of the bottom DBR layer and is formed in a position facing the upper DBR layer of the upper mirror part via a gap; a DBR layer formed on the active layer; and a driving part for changing a cavity length of a cavity formed between the DBR layer on the active layer and the upper DBR layer by driving the oscillation part in the diaphragm.

The driving part may be a parallel plate type and drives the diaphragm by electrostatic force.

The driving part may be a driving plate using the bimorph effects by heat.

According to the present invention having such features, oscillation wavelength can be continuously changed with high speed by continuously changing the cavity length of the surface emission laser. Since the surface emission laser oscillates in a single mode in principle, detection sensitivity to an interference signal is high, and internal detectable depth is great. For this reason, a motion image can be displayed with high sensitivity.

BRIEF DESCRIPTION OF THE DRAWINGS

FIG. 4A is a view showing a change of a transmission factor against an oscillation frequency of a slope filter in the wavelength monitor according to this embodiment.

FIG. 4B is a view showing a change of an output from a photodiode against the oscillation frequency.

FIG. 5 is a graph showing an oscillation frequency and temporal change.

FIG. 6A is a top view of an upper substrate of an emission laser in the tunable light source according to embodiment 2 of the present invention.

FIG. 6B is an end view in A-A line of the upper substrate in this embodiment.

DESCRIPTION OF THE PREFERRED EMBODIMENTS

Figure 1:
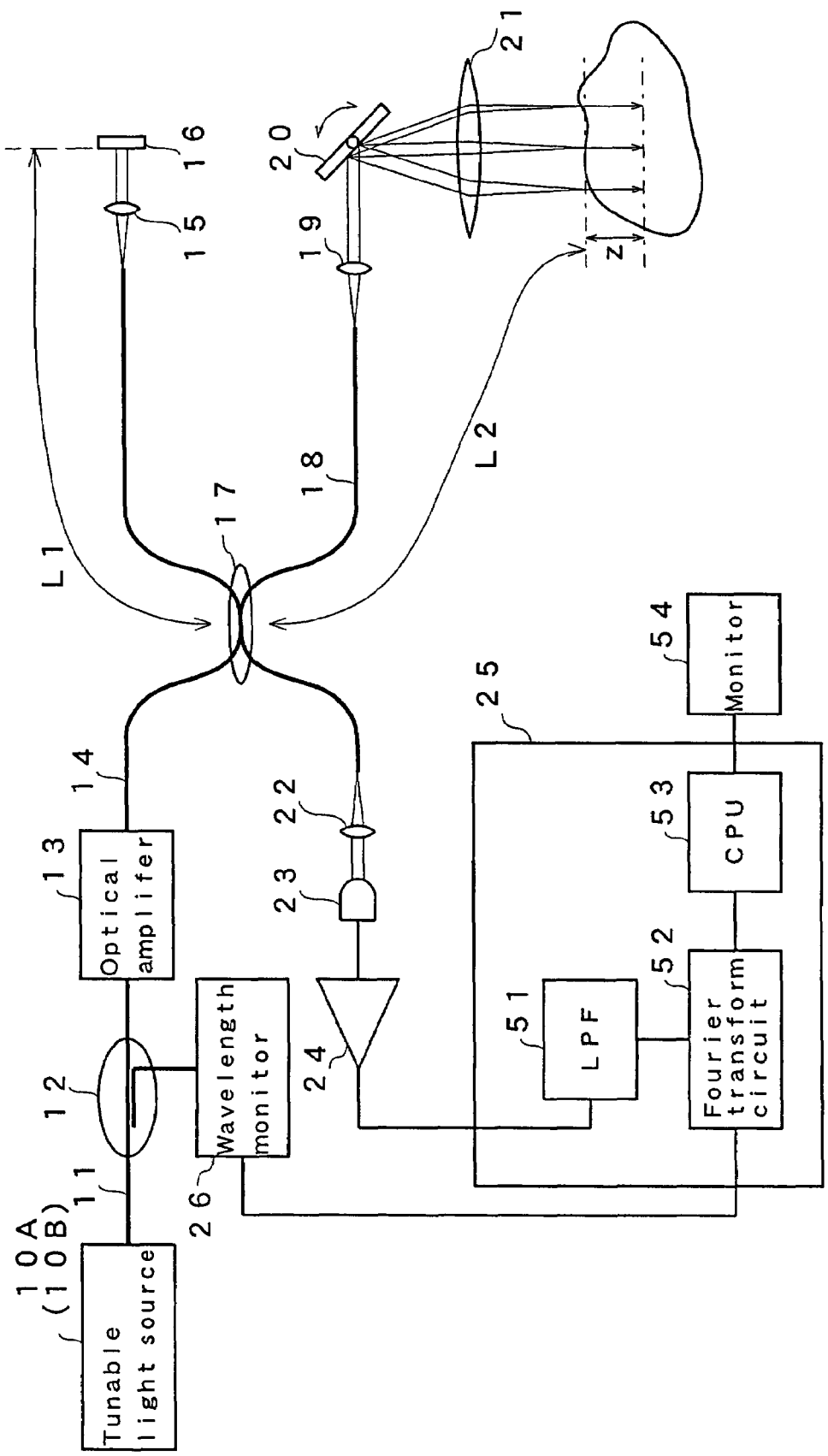
FIG. 1 is a block diagram showing an entire configuration of a wavelength scanning type optical tomography system according to embodiment 1 of the present invention.

FIG. 1 is a block diagram showing an entire configuration of a tunable optical coherent tomography system according to embodiment 1 of the present invention. In the figure, a tunable type surface emission laser which emits a light signal within a certain frequency range is used for a tunable light source 10A. An output of the surface emission laser is given to a division part 12 through an optical fiber 11. An optical amplifier 13 is provided to the other end of the optical fiber 11. The optical amplifier 13 amplifies laser light from the tunable light source 10A as it is, and the output is given to an optical fiber 14. A collimate lens 15 and a reference mirror 16 are provided to the other end of the optical fiber 14. In addition, a connecting part 17 for bringing other optical fiber 18 near the optical fiber 14 and for making the optical fiber 18 interfere with each other is provided in a middle portion of this optical fiber 14. A collimate lens 19 and a scanning mirror 20 for scanning light are provided to one end of the optical fiber 18. The collimate lens 19 collimates light signals obtained from the tunable light source 10A via the connecting part 17. The scanning mirror 20 changes a reflection angle of the collimated light by rotating centering around an axis vertical to the paper within a determined range. A focusing lens 21 is arranged at a position where the focusing lens 21 can receive this reflecting light, and executes scanning in a horizontal direction with focusing the light to a measurement area. An optical path length L1 from the connecting part 17 to the reference mirror 16 and an optical path length L2 from the connecting part 17 to a surface of a measurement area are equalized here. A photodiode 23 is connected to other end of the optical fiber 18 via a lens 22. The photodiode 23, that is a light receiving element, obtains a beat signal as an electric signal by receiving interference light made of a reflecting light from the reference mirror 16 and a light reflected on a measurement area. The optical fibers 14 and 18, the connecting part 17, the collimate lens 15, the reference mirror 16, the collimate lens 19, the scanning mirror 20, and the focusing lens 21 compose an interferometer.

And now, an output of the photo diode 23 is inputted to a signal processing part 25 via an amplifier 24. The signal processing part 25 obtains a tomography image signal by executing the Fourier transform to a received signal obtained from the interference device as described below.

A part of an output from the tunable light source 10A is divided by the division part 12, and is given to a wavelength monitor 26. The wavelength monitor 26 generates a lot of k trigger signals within one scanning by a light of the tunable light source and at even frequency interval as described below. This k trigger signal is inputted to the signal processing part 25.

Figure 2:
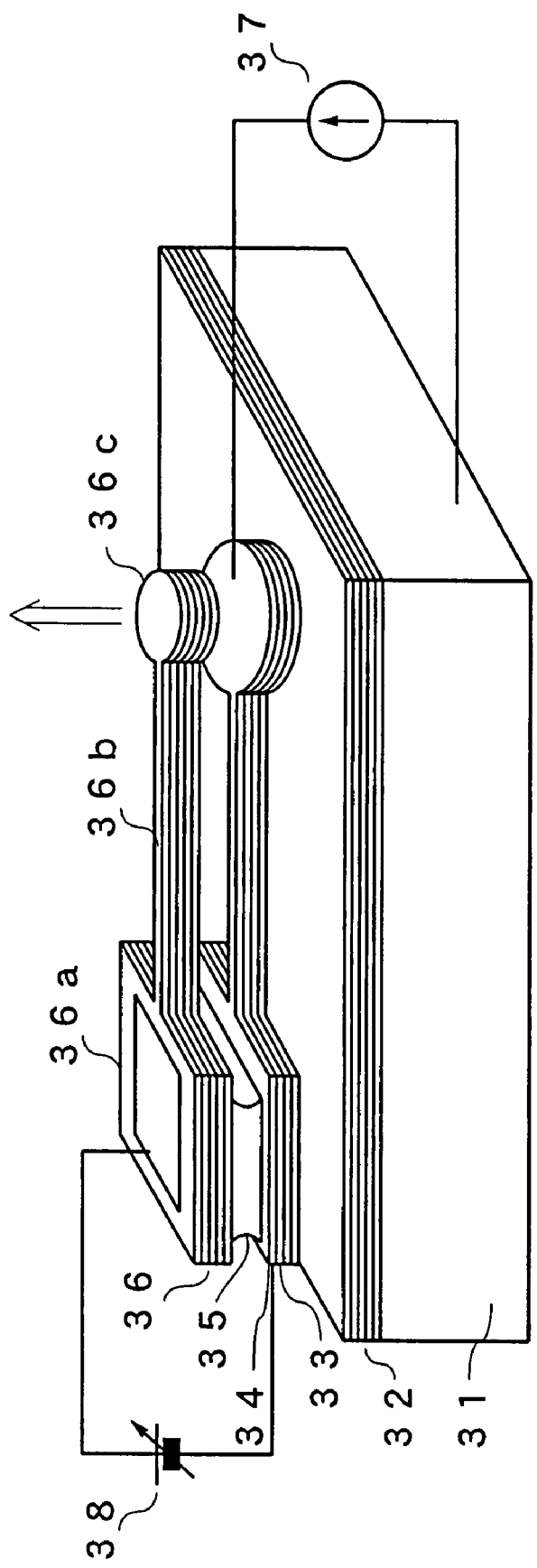
FIG. 2 is a schematic diagram showing a tunable light source according to the present embodiment.

Next, regarding the tunable light source 10A used in embodiment 1, the surface emission laser that is a main component thereof will be mainly explained. As shown in a perspective view of FIG. 2, the surface emission laser arranges an n-doped distributed Bragg reflection mirror (DBR) 32 being composed of semiconductor multilayer film on a substrate 31 such as GaAs. The DBR layer 32 is composed of high refractive index layers and low refractive index layers, for example, $TiO_2$ and $SiO_2$ having thicknesses of $\lambda/4$, respectively are laid alternately, where the $\lambda$ represents an optical path length of an oscillation wavelength. The DBR layer 32 constitutes a downward mirror surface in a vertical cavity. Then, an active layer 33 having a multiquantum well structure and a p-doped DBR layer 34 are formed on its top. The structure of the DBR layer 34 is same as that of the DBR layer 32. The active layer 33 and the p-doped DBR layer 34 have a shape formed by jointing a square part and circle part with a joining part as shown in the figure. And, a sacrifice layer 35 and a DBR layer 36 are provided on the top of the square part. The sacrifice layer 35 is formed on the p-doped DBR layer 34, and the DBR layer 36 is formed on the sacrifice layer 35. The DBR layer 36 composes a movable reflecting part by etching the sacrifice layer 35. The DBR layer 36 consists of a rectangular part 36a formed on the top of the sacrifice layer 35, a beam part 36b, and a circular part 36c as also shown in the figure. The beam part 36b is a cantilever beam, and holds the circular part 36c almost parallel to the DBR layer in up-and-down direction so that the DBR part 36c can be movable. The circular part 36c is an n-doped DBR layer. And, a vertical type cavity is composed of the circular part 36c and the bottom DBR layer 32. An electric current source 37 is provided between the substrate 31 and the DBR layer 34, and an alternating electric voltage source 38 for changing wavelength is connected between a contact provided to the upper rectangular part 36a and the DBR layer 34. The DBR layer 34 is parallel to the circular part 36c and configures a driving part for driving the circular part 36c by using electrostatic force.

Here, electric current is filled into the active layer 33 by applying electric current between the substrate 31 and the p-doped DBR layer 34 from the electric current source 37. Hereby, excited photons resonate in the vertical cavity, and oscillate at a frequency matched with the Fabry-Perot mode of the cavity within a gain range of the active layer 33. Laser is partially reflected on the DBR layer 34 on the active layer 33 here, and a part of the light excited in the active layer 33 passes out of its upper layers to air. By setting a cavity length between the upper DBR layer and the bottom DBR layer to be a few μm, oscillation in longitudinal mode that is one of the Fabry-Perot mode arises. As a result, the surface emission laser, in principle, oscillates in the single mode. Further, the voltage source 38 applies reverse bias voltage $V_{tune}$ between the movable n-doped circular part 36c and the p-doped DBR layer 34. As the voltage $V_{tune}$ changes, a reflection phase changes because a gap of the cavity part changes by the electrostatic force. Hereby, a wavelength of the resonator changes, and as a result of this, a wavelength of an excited laser changes.

Figure 3:
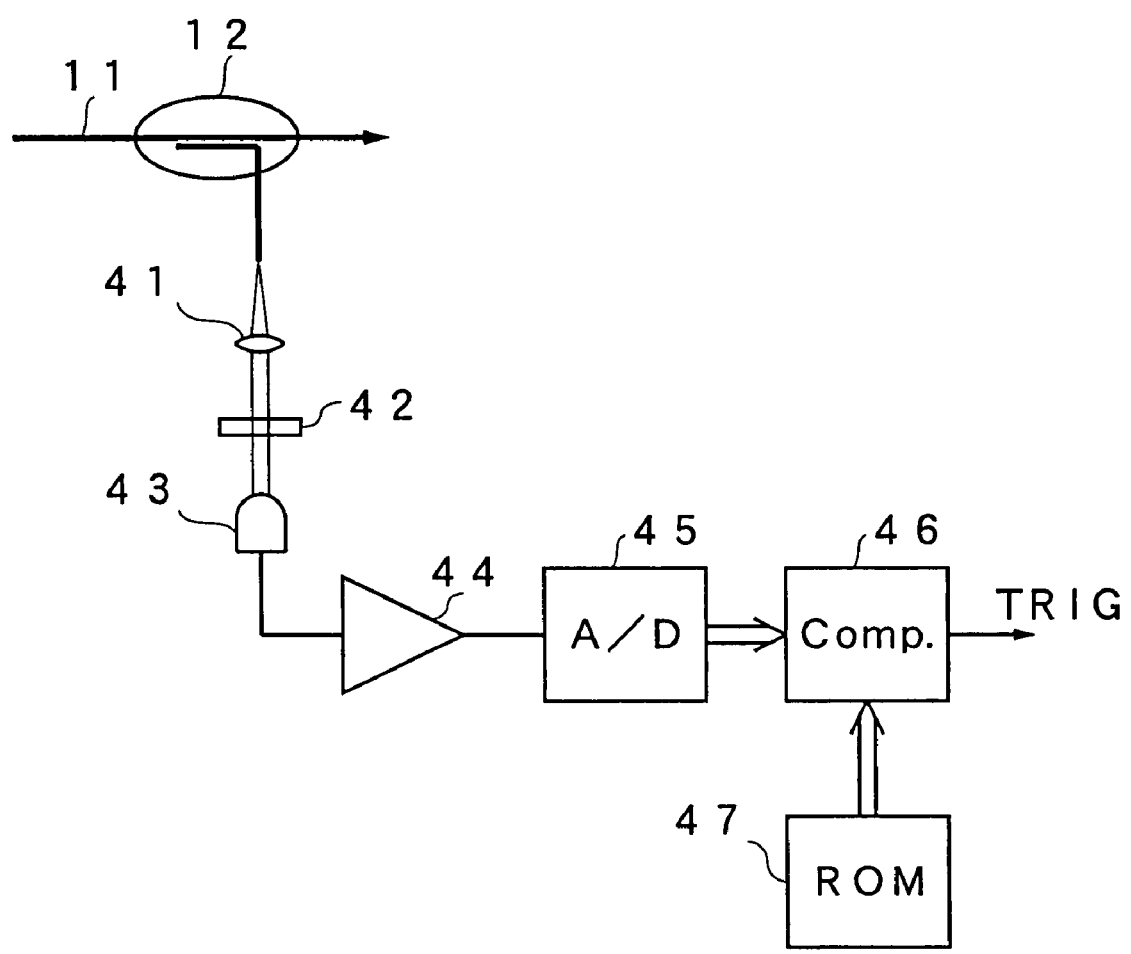
FIG. 3 is a block diagram showing a configuration of a wavelength monitor according to the present embodiment.

Next, the wavelength monitor 26 will be explained using FIG. 3. The division part 12 divides the laser output of the tunable light source 10A and inputs a part of it to the wavelength monitor 26. The wavelength monitor 26 includes a collimate lens 41 for collimating a divided light, a slope filter 42, and a photodiode 43 for receiving transmission light. The slope filter 42 is a filter whose transmission factor linearly changes against optical frequency as shown in FIG. 4A. The photodiode 43 gives an output thereof to an A/D converter 54 via an amplifier 44. The A/D converter 54 converts the output to a digital value, and the output is given to a comparator (Comp.) 46. The comparator 46 compares a calibration value stored in a ROM 47 with an output of A/D conversion, and generates a k trigger signal (TRIG) when two inputs equal out. The ROM 47 retains voltages corresponding to A/D conversion outputs V1, V2, V3, ... corresponding to equal frequency interval as a calibration values as shown in FIG. 4B. In this way, the k trigger signal is generated in the equal frequency interval of oscillation frequency, and is given to the signal processing part 25.

Next, a configuration of the signal processing part 25 will be explained using FIG. 1. An output of the amplifier 24 is given to a low-pass filter (LPF) 51 to eliminate high-frequency component in the output, and is inputted to a Fourier transform circuit 52. The Fourier transform circuit 52 executes the Fourier transform to output of the low-pass filter 51 based on a trigger signal from the wavelength monitor 26, and its outputs are transferred to a CPU 53. In response to this, the CPU 53 executes a signal processing described below, and transfers the processed outputs to a monitor 54 as image signals.

Next, a principle of the optical coherent tomography using the tunable light source will be explained. A coherent light whose optical frequency changes continuously and periodically is emitted to a target object from a light source, and interference of a reference light and a backscattered light reflected at interior of an object or on lower epidermis of a living body is made by using an interferometer such as the Michelson or the Mach-Zehnder. A tomography image along a depth direction can be structured through the intensity distribution corresponding to a shift of an optical frequency. Further, by scanning a spatial beam on the object in one and two-dimension, two-dimensional and three dimensional tomography images are structured respectively.

When optical paths of two arms from the connecting part 17, that is, an optical path L1 to the reference mirror 16 and an optical path L2 to a reflection plane in the object are equal in the interferometer, a beat frequency of interference light is zero. If an optical frequency changes when an incident light is reflected at a depth z in the object, beats arise in the interference light because a difference in a frequency of the reflecting light from the object and the reflecting light from the reference mirror 16 causes in accordance with a degree of their optical path difference. Here, for example, an optical frequency of a light source is assumed to be scanned time-linearly. It is assumed that a surface of the object exists at a position where arms of the interferometer are equivalent length, and a reflection plane of the object only exists at a position of depth z from the surface. Temporal change of a frequency of a reference light and a frequency of a reflecting light (object light) from an object at the connecting part 17 are shown as a line A and line B respectively in FIG. 5. The optical frequency is scanned at a scanning rate α [Hz/s] and for frequency width Δf=α T [Hz] within a time T [s] here. When a refraction index of the object is n, a delay time τ of the object light against the reference light is shown as:

$$\tau = 2nz/c.$$

As a result, an interference light received by the photodiode 23 fluctuates in a beat frequency shown as:

$$fb = \alpha\tau = (\Delta f/T)(2nz/c) \quad (1).$$

Actually, since reflecting lights arise at differential positions continuously along internal depths of an object, the reflecting lights have different beat frequency components corresponding to each depth.

Therefore, intensity of reflecting light from a certain depth corresponding to a beat frequency can be detected by executing frequency analysis for intensity change of an interference light. A tomography image can be structured by plotting a special distribution of this reflecting intensity.

Mathematically, this frequency analysis is obtained by executing the Fourier transform for interference optical signal $I_{dct}$ shown in the following expression (2):

$$I_{dct} = (\eta q/h\nu)\{Pr + Po\int r(z)dz + 2(PrPo)^{1/2}\int r(z)\cos(2k(t)z + \phi)dz\} \quad (2).$$

The first and second terms mean direct-current components from a reference mirror and a reflecting light from an object, respectively, and the third term means a component of an interference light signal. In the expression (2), the Pr represents intensity of a reference light, Po represents intensity of a probe light, and r(z) represents a reflectance distribution in a depth direction. By executing the Fourier transform for the interference light signal of $I_{dct}$ obtained by the expression (2), a relation of intensity of scattered lights corresponding to arbitrary depths in an object can be obtained.

Interference optical signal is as follows:

$$F(z) = \Sigma I_{dct}[k_m]\exp(-j2k_m z_n) \quad (3),$$

$$k_m = k(t_m) = 2\pi/\lambda(t_m) = 2\pi f(t_m)/c.$$

A distortion-free image can be obtained by executing the Fourier transform for above-described interference light signal at even sampling in a k space. A trigger signal giving a timing of this sampling needs to be synchronized with a light frequency that the tunable light source 10 scans, and in addition, needs to be even on wave number, that is, a frequency domain.

A resolution δ z in a direction of a depth is in proportion to an inverse of a scanning range and is shown as an expression (4):

$$\delta z = (2 \ln 2/\pi)(\lambda_0^2/\Delta\lambda) \quad (4),$$

where $\lambda_0$ represents a central wavelength and $\Delta\lambda$ represents a wavelength scanning range. That is to say, the wider scanning range becomes, the higher the resolution is.

Next, a coherent length Lc is shown as follows:

$$Lc = (2 \ln 2/\pi)(C/\Delta\nu) \quad (5),$$

where Δν represents a dynamic line width, that is, a spectrum line width when the wavelength shifts. The coherent length Lc is equivalent to double measuring length in a depth direction, and becomes wider in inverse proportion to the line width. Accordingly, it is preferable for an image display system to include a tunable light source having a wide wavelength scanning range and a narrow line width (high coherent). The tunable light source 10A of a surface emission laser oscillating in the single mode is used in the present invention. As a result, since a line width is more than a few MHz and a coherent length is longer than that of a laser in multi-mode oscillation, measuring depth in the OCT can be deepened and a deep measuring range can be displayed.

Next, an operation of the present embodiment will be explained. As described above, a signal light is emitted up to a reference mirror and an object via an optical fiber by driving the tunable surface emission laser 10, the reflecting light can be obtained via the connecting part 17. The photodiode 23 detects the beat frequency signal and feeds the beat frequency signal to the signal processing part 25 after amplified. In addition, as described above, the wavelength monitor 26 generates trigger signals in equal frequency interval. The signal processing part 25 generates a tomography image by executing the Fourier transform for an output of the photodiode 23 on the basis of these trigger signals. Then, the scanning mirror 20 changes the incidence position of light as rotating, and whereby, two-dimensional tomography image can be obtained. In addition, three-dimensional tomography image can be obtained by vertically moving this interference device or a measuring object against a scanning direction of light from the scanning mirror 20.

Subsequently, embodiment 2 of the present invention will be explained. In embodiment 2, only a tunable light source is different from that in embodiment 1, and other components are the same as those of embodiment 1 described above.

Figure 7:
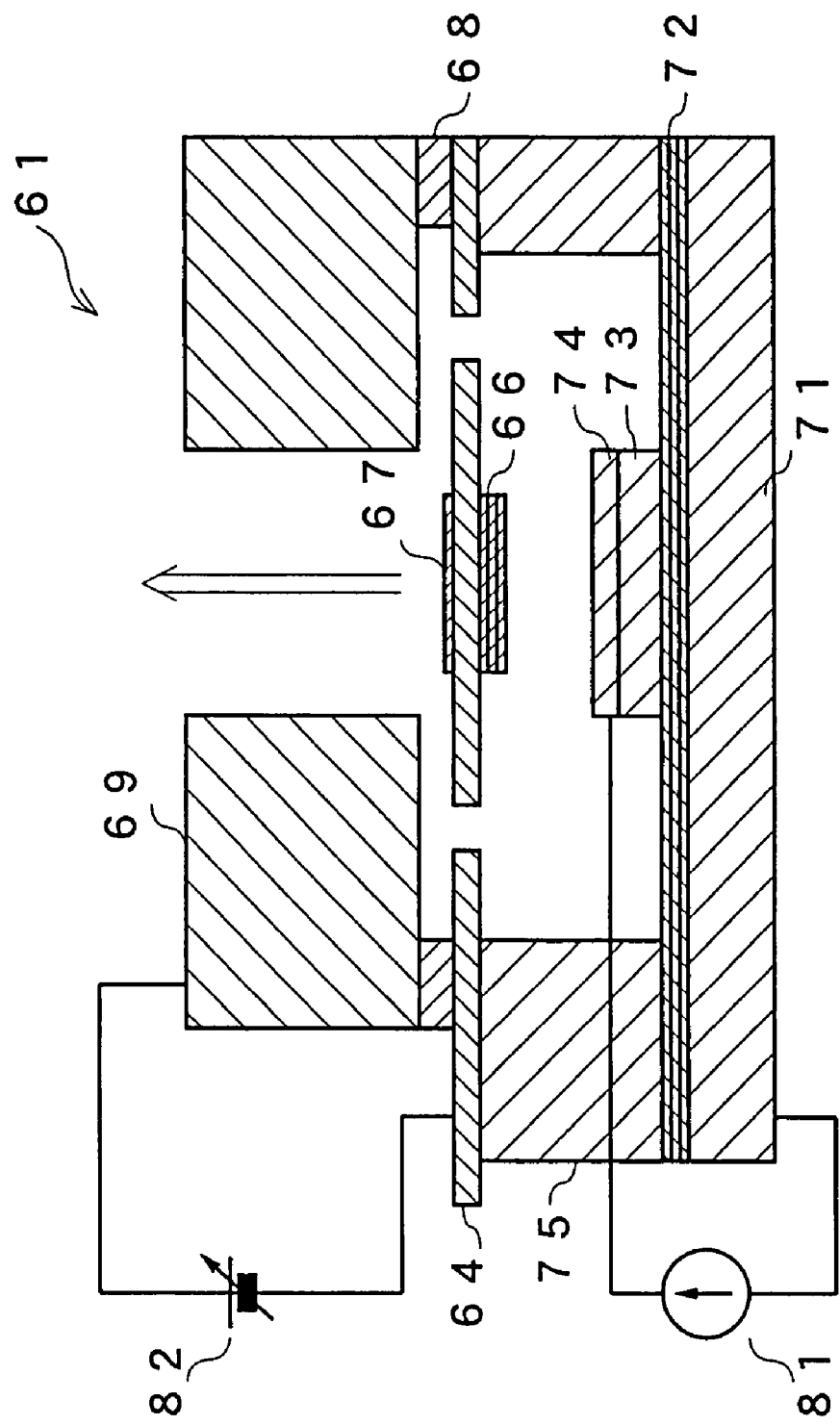
FIG. 7 is an end view showing a entire configuration of the tunable light source in this embodiment.

FIG. 6A is a top view showing a vertically movable mirror part of a surface emission laser in the tunable light source 10B according to embodiment 2, and FIG. 6B is an end view in A-A line thereof. FIG. 7 is an end view showing an entire configuration of the tunable light source. As shown in the figures, a surface emission laser 61 in the tunable light source is composed of an upper mirror part 62 and a bottom substrate. This surface emission laser is manufactured by bonding an independently manufactured mirror part 62 to the bottom substrate. The mirror part 62 includes a thin rectangle diaphragm 64 made of Si layer. A circular vibration part 64a of the diaphragm is supported via four hinges 65 so as to vibrate. A distribution type Bragg reflector (DBR) layer 66 having high reflectance is formed in circular form on the vibration part 64a of the diaphragm 64. The DBR layer 66 is a high reflectance layer structured in a multi-layer structure with an optical path length of λ/4, and an AR coat layer 67 is provided on its backside. In addition, a handle substrate 69 which is composed of Si layer is provided around the diaphragm 64 via an insulation layer 68 made of SiO$_2$. The handle substrate 69 has an opening in a central portion by getting rid of the portion corresponding to the DBR layer 66 and faces the diaphragm 64 apart via a gap of a thickness of the insulation layer 68. The handle substrate 69 is parallel to the diaphragm 64 and configures a driving part for driving the diaphragm 64 by using electrostatic force.

In the bottom substrate, an n-doped bottom DBR layer 72 is provided on a substrate 71 of InP or GaAs as shown in FIG. 7. A circular active layer 73 having a quantum well structure is provided on the upper surface of the bottom DBR layer 72. In addition, a p-doped DBR layer 74 is provided on the top of the active layer 73. A spacer 75 having a circular opening centering around this active layer 73 is arranged on the top of the bottom DBR layer 72. Further, above mentioned movable mirror part 62 is arranged on the spacer 75 setting the upper DBR layer 66 to be bottom surface so as to face the DBR layer 74 parallel via a gap.

As shown in FIG. 7, an electric current source 81 for current injection is connected with the DBR layer 74 and substrate 71. In addition, an electric voltage source 82 is connected with the diaphragm 64 of the movable mirror and with the handle substrate 69. A voltage of the voltage source 82 changes a cavity length of a cavity part in the diaphragm 64 by using the electrostatic force, and is an alternating-current source for realizing a wavelength scanning.

By injecting an electric current from the electric current source 81 to the active layer 73, laser is oscillated in a wavelength corresponding to the Fabry-Perot mode in the cavity between the upper DBR layer 66 and the bottom DBR layer 72. This laser light is outputted upward from a center portion of the handle substrate 69. Here, a voltage $V_{tune}$ is applied between the handle substrate 69 and the diaphragm 64, and is changed. Then a position of the diaphragm 64a can be changed in up-and-down direction by electrostatic force, and a wavelength of laser oscillation can be changed by changing the cavity length.

The tunable light source 10B can be simply designed because a cavity length of a surface emission laser and a gap for electrostatic force can be independently configured. In addition, the range of wavelength can be wide in the light source, while the range of wavelength is narrow in a monolithic process using only a semiconductor.

In addition, in both of the surface emission lasers shown in embodiments 1 and 2, cavities are formed by using a plane type DBR layers, and wavelengths are changed depending on change of the cavity lengths by electrostatic force. In stead of the electrostatic force, a plurality of thermal stress layers that have independent thermal expansion coefficients may be provided to either of DBR layers, and the DBR layer may be displaced by changing temperature. In this manner, a cavity length of a cavity is changed by the bimorph effects, and a wavelength can be changed. In addition, a surface emission laser which changes a cavity length by using a vertical comb-shaped actuator may be used.

What is claimed is:

1. An optical tomography system comprising:
   a tunable light source including a tunable surface emission laser for generating laser light and periodically scanning an oscillation wavelength of light;
   a wavelength monitor for generating trigger signals in equal frequency interval of light of said tunable light source within a period of one scanning of said tunable light source;
   an interferometer for dividing the light from said tunable light source into a reference light and an emission light, and for generating interference light of reflecting light from an object and the reference light;
   a light receiving element for receiving interference light from said interferometer and for obtaining a beat signal; and
   a signal processing part for forming a tomography image of said object by executing the Fourier transform synchronizing a timing with an output from said light receiving element and the trigger signal from said wavelength monitor;
   wherein said tunable surface emission laser includes:
   a bottom DBR layer formed on a substrate;
   an active layer formed on said bottom DBR layer;
   a DBR layer formed on said active layer;
   a movable DBR layer of a cantilever structure formed over said active layer via a gap; and
   a driving part for driving said movable DBR layer and for changing a cavity length of a cavity formed between said DBR layer on said active layer and the movable DBR layer.

2. The optical tomography system according to claim 1, wherein said driving part is a parallel plate type and drives said diaphragm by electrostatic force.

3. The optical tomography system according to claim 1, wherein said driving part is a driving plate using the bimorph effects by heat.

4. The optical tomography system according to claim 1, further comprising: an optical amplifier for amplifying an optical output of said tunable light source.

5. An optical tomography system comprising:
- a tunable light source including a tunable surface emission laser for generating laser light and periodically scanning an oscillation wavelength of light;
- a wavelength monitor for generating trigger signals in equal frequency interval of light of said tunable light source within a period of one scanning of said tunable light source;
- an interferometer for dividing the light from said tunable light source into a reference light and an emission light, and for generating interference light of reflecting light from an object and the reference light;
- a light receiving element for receiving interference light from said interferometer and for obtaining a beat signal; and
- a signal processing part for forming a tomography image of said object by executing the Fourier transform synchronizing a timing with an output from said light receiving element and the trigger signal from said wavelength monitor;

wherein said tunable surface emission laser includes an upper mirror part and a bottom substrate, said upper mirror part includes:
- a diaphragm having an oscillation part supported by hinges;
- an upper DBR layer provided on said diaphragm for reflecting light; and
- a handle substrate which faces said diaphragm via a spacer and is formed in circular shape getting rid of a part of said upper DBR layer, and said bottom substrate includes:
- a bottom DBR layer;
- an active layer which is provided on a top of said bottom DBR layer and is formed in a position facing the upper DBR layer of said upper mirror part via a gap;
- a DBR layer formed on said active layer; and
- a driving part for changing a cavity length of a cavity formed between said DBR layer on said active layer and said upper DBR layer by driving said oscillation part in said diaphragm.

6. The optical tomography system according to claim 5, wherein said driving part is a parallel plate type and drives said diaphragm by electrostatic force.

7. The optical tomography system according to claim 5, wherein said driving part is a driving plate using the bimorph effects by heat.

* * * * *